United States Patent [19]

Bradley et al.

[11] Patent Number: 4,766,740
[45] Date of Patent: Aug. 30, 1988

[54] CONTAINER FOR THE PRESERVATION AND TRANSPORTATION OF SEVERED LIMBS OR OTHER BODY PARTS

[75] Inventors: Laurie Bradley, 55 Alpine Avenue, Surbiton, Surrey; Richard J. Lilleystone, 32 High Pine Close, Weybridge, Surrey; Clive S. Cumner, Surrey, all of England

[73] Assignees: The Distillers Company (Carbon Dioxide) Limited, Reigate; Laurie Bradley, Surbiton; Richard J. Lilleystone, Weybridge, all of England

[21] Appl. No.: 81,388

[22] Filed: Aug. 4, 1987

[30] Foreign Application Priority Data

Aug. 8, 1986 [GB] United Kingdom ............... 8619437

[51] Int. Cl.⁴ ............................................. F25D 3/12
[52] U.S. Cl. ......................................... 62/384; 62/388; 62/457
[58] Field of Search ............... 62/384, 386, 388, 306, 62/457

[56] References Cited

U.S. PATENT DOCUMENTS

| | | | |
|---|---|---|---|
| 1,903,171 | 3/1933 | Cordrey | 62/388 X |
| 3,914,954 | 10/1975 | Doerig | 62/306 |
| 3,922,878 | 12/1975 | Jalali | 62/384 |
| 4,288,996 | 9/1981 | Roncaglione | 62/384 |
| 4,462,215 | 7/1984 | Kuraoka et al. | 62/306 X |
| 4,606,195 | 8/1986 | Winkler | 62/384 X |

Primary Examiner—Lloyd L. King
Attorney, Agent, or Firm—Sughrue, Mion, Zinn, Macpeak and Seas

[57] ABSTRACT

A container for transporting an accidentally severed limb 17 or other body part and keeping it cool to aid the success rate of replantation surgery comprising a suitcase-like openable container 2 made of aluminium sheet 4 with a heat insulating covering 5. To maintain the temperature of the container between 2° C. and 6° C., a cylinder of carbon dioxide 19 is mounted in a holder 9, 18 on the outside of the container and has its shut-off valve 20 connected to an injector nozzle 23 in the container. Carbon dioxide discharged by the nozzle 23 produces dry ice in the container 2 to cool it. The flow of gas through the nozzle 23 is controlled by a thermostatic device which includes a spring 24 made of a shape-memory alloy which allows the nozzle 23 to be closed at temperatures below 2° C. but which regains its strength at a temperature of 6° C. to open the nozzle when the insider of the container has warmed up again to this temperature.

19 Claims, 2 Drawing Sheets

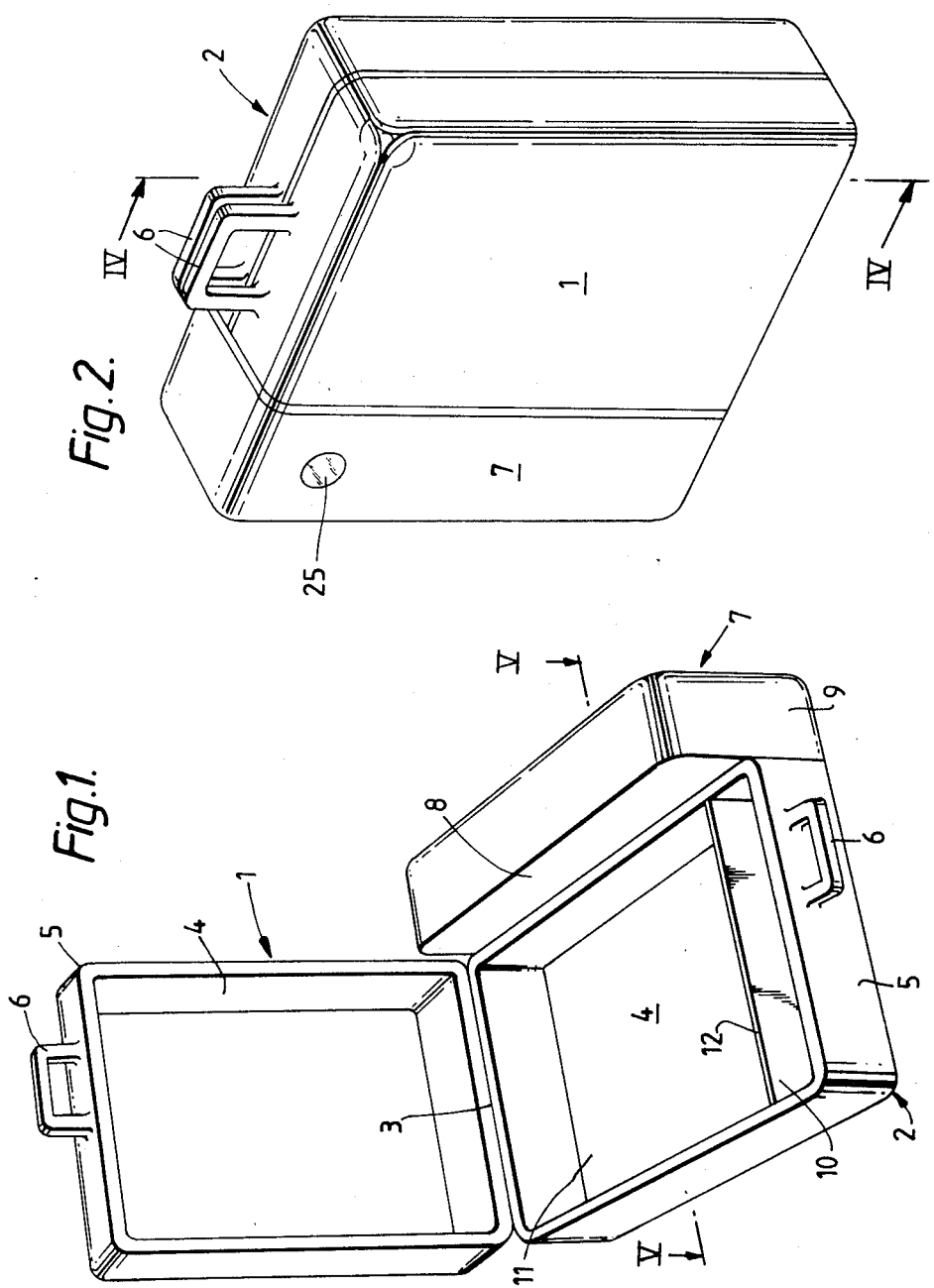

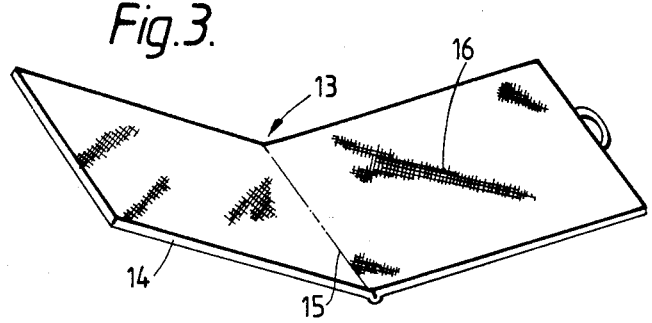
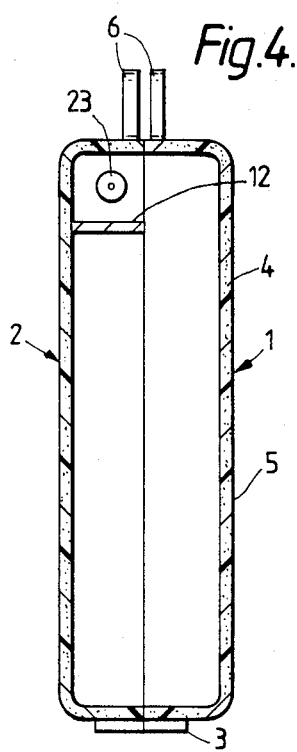
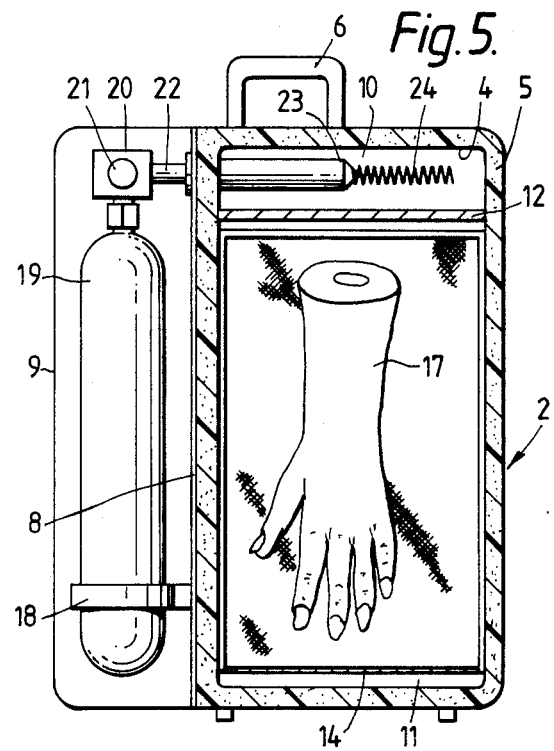

CONTAINER FOR THE PRESERVATION AND TRANSPORTATION OF SEVERED LIMBS OR OTHER BODY PARTS

BACKGROUND OF THE INVENTION

If a limb or other body part is severed from the body in any way, for example by an accident in which the body part is trapped in a piece of moving machinery, it is nowadays frequently possible to replant the body part using micro-surgical techniques. The success of such surgical operations is, however, greatly dependent upon the condition of the body part when the surgery takes place. It has been found that the success rate is greatly improved if the body part is kept cool, and preferably at a temperature of from 0° to 8° C. and more preferably between 2° and 6° C. for as much as is possible of the time between severance and the surgical replantation. It is also most helpful to protect the body part and reduce shock and trauma.

The present invention is thus concerned with a portable container, for transporting a severed limb or other body part and keeping it cool during transport, the container comprising an openable housing having heat insulated walls and a removable holder for holding a body part within the housing.

A portable container such as this is disclosed in FR-A No. 2560/64. This container is in the form of a heat insulated box, which has a screw top and heat insulated walls. In use, the box is filled with ice and water and a body part, such as a finger is inserted in a flexible bag and is immersed in the iced water through a hole in the screw top.

This arrangement is exceedingly cumbersome and therefore not all practical. Because of the balance of iced water, which is heavy the box can only be big enough to hold a small body part such as a finger or toe, or else it can no longer be portable. Also, there is no positive temperature control. The temperature of the bag is maintained at 0° C., which is a little too low, until all the ice melts and after that it rises uncontrollably.

SUMMARY OF THE INVENTION

According to this invention, a container as described above is characterised by a rechargeable cylinder of compressed carbon dioxide mounted within, or on the outside of, the housing, the cylinder having a shut-off valve and an injector nozzle within, or in communication, with the inside of the housing for injecting carbon dioxide coolant into the housing, which is vented to atmosphere, and producing dry ice or expanded and cooled gas within the housing, the gas flow through the injector nozzle being controlled by a thermostatic device to maintain the temperature in the housing within predetermined limits.

Preferably the container is in the general form of a suitcase with an external compartment for holding the gas cylinder fixed to one side.

Although the walls of the container must be heat insulated as already mentioned, the inside faces of the walls of the container are preferably heat-conducting to act as a heat sink and ensure that the heat extracted by the cooled gas it withdrawn from the whole of the container so that the space within it is maintained at a substantially uniform temperature.

For this purpose, the container preferably consists of two trays of sheet metal which has a relatively high coefficient of heat conductivity. The trays are preferably of aluminium or of aluminium alloy. The insulation of the walls of the trays preferably then consists of high-density plastics foam moulded onto and covering the whole of the outside surface of each of the trays. The high-density foam is preferably covered with an impervious skin of plastics material in much the same way as the dashboards and some other parts of the interior of motor cars are customarily padded with foamed plastics material as a safety measure.

The compartment which holds the carbon dioxide cylinder may have a steel or other metal base-plate which is fixed to one side of one of the trays and to which a clamp or other holder for the gas cylinder is fixed. The metal base-plate is provided with a cover, which may be injection moulded out of thermoplastics material such as polypropylene and which is shaped to form an extension of the surface of the two foamed plastic covered aluminium trays when these are closed together.

A fitting for receiving the shut-off valve of the carbon dioxide cylinder is provided at one end of the compartment and a tube with an injector nozzle at its end extends from this fitting through the base-plate of the compartment and through the side wall of the tray to which the compartment is fixed into the inside of this tray. To prevent dry ice impinging directly upon a severed limb or body part within the container, a baffle, which may also be made of aluminium or aluminium alloy may be disposed adjacent the injector nozzle to separate this from direct communication with the remainder of the inside of the housing. The cover of the cylinder compartment preferably has an opening through which the shut-off valve of the cylinder is manually accessible.

The holder for the limb may consist of a frame having two parts which are hinged together with each part supporting a network or mesh panel so that when the two parts of the frame are closed together, a limb may be sandwiched between the two mesh panels. Both the two parts of the frame and the mesh panels may be made of plastics material and the holder can be removed from the housing with the limb held between the two panels to enable the limb to be taken to an X-ray machine or for other examination without it being necessary to handle the limb itself.

Preferably the carbon dioxide cylinder is of the syphon tube type, which has a tube extending from its outlet into the cylinder with its open end adjacent the opposite end of the cylinder so that with the open end of the tube lowermost, liquid carbon dioxide issues from the cylinder when the shut-off valve is open. The liquid carbon dioxide is expanded through the injector nozzle into the compartment within the housing on one side of the baffle when the shut-off valve is opened.

The thermostatic device may include a solenoid valve for controlling the gas flow through the nozzle and a temperature sensor in a circuit controlling the valve. Preferably however the thermostatic device is mechanically operated and incorporates a spring made of shape memory alloy, which is a material which, when heated to a predetermined temperature, which itself depends upon the composition of the alloy, returns from a deformed state to a previously "memorised" state and in so doing operates a control member, which controls the flow of gas from the injector nozzle. Since, as already mentioned, the interior of the container is preferably maintained between 2° and 6° C., the thermostatic device is preferably arranged to open the injector nozzle when the temperature within the container rises to 6° C. and to close it again when the temperature has dropped to 2° C.

The opening in the cover of the cylinder compartment through which the control member of the shut-off valve is manually accessible may be provided with a seal in the form an identity tag or ring. To open the valve, the identity tag or ring must first be removed and the tag or ring is then fixed to the patient from whom a limb or other body part has been severed and this tag or ring then provides a cross-reference with a number on the container in which the severed limb is taken to hospital.

In some cases it may also be desirable to fit a small elapsed time clock to the container and this is preferably battery powered. The elapsed time clock is set in operation as soon as the severed limb or body part is placed in the container and this, of course, is as soon as possible after severance has taken place. It is also in some cases desirable to provide the container with an externally visible temperature indicator.

BRIEF DESCRIPTION OF THE DRAWINGS

An example of a container in accordance with the invention is illustrated diagrammatically in the accompanying drawings in which:

FIG. 1 is a front perspective view of the container open and ready to receive a severed limb;

FIG. 2 is a perspective view of the container closed as seen from the top and from one side;

FIG. 3 is a perspective view of a detachable holder for holding a severed limb within the container;

FIG. 4 is a vertical section through the closed container as seen in the direction of the arrows on the line IV—IV in FIG. 2; and, FIG. 5 is a sectional view through one half of the container as seen in the direction of the arrows on the line V—V in FIG. 1.

DETAILED DESCRIPTION OF THE PREFERRED EMBODIMENTS

The container is formed in two similar parts 1 and 2 which are connected together by a hinge 3. Each of the two parts 1 and 2 comprises a rectangular tray 4 formed of sheet aluminium and an outer covering of rigid high-density plastics foam insulating material 5. Handles 6 are provided for ease of transportion.

Fixed to one side of the part 2 is a compartment 7 which has a sheet steel base plate 8 and a moulded cover 9.

The inside of the part 2 is divided into two compartments 10 and 11 by a baffle 12, which is also of sheet aluminium.

A holder 13, which is shown in FIG. 3, fits detachably within the compartment 11 and, when it holds a limb, extends upwards into the part 1 of the container when the container is closed. The holder 13 comprises a frame 14, which is injection moulded out of plastics material in two parts which are hinged together along a hinge line 15. A panel 16 of flexible plastics mesh material is held in the frame 14 so that a limb such as a hand and wrist 17, as shown in FIG. 5, may be held between the two parts of the panel 16 when the two parts of the frame 14 are closed together.

A clamp-like holder 18 is fixed to the base-plate 8 and holds a carbon dioxide cylinder 19. The cylinder 19 has a shut-off valve 20 which is manually operated by a handle 21. An outlet tube 22 leads from the valve 20 into the compartment 10 where it is fitted with an injector nozzle 23. The flow of gas through the injector nozzle 22 is controlled, when the valve 20 is open, by a thermostatic device, which is actuated by a spring 24 made of a shape memory alloy.

When the container is closed as shown in FIG. 2, the handle 21 of the valve 20 is accessible through an opening 25 in the bottom of the cover 7.

In use, when a limb, such as the hand 17 is severed from a patient, the container is at once taken to the limb as quickly as possible and with the part 2 placed on a horizontal support, the container is opened as shown in FIG. 1. The holder 13 is then opened and the limb 17 is placed on the lower half of the panel 16 after which the holder 13 is closed again so also is the container itself. The container is held shut by a catch, which is not shown, but which is located between the handles 6.

As soon as the container is closed and stood in an upright position as shown in FIG. 2, the valve 20 is opened and liquid carbon dioxide flows from the cylinder 19, which is of the syphon tube type, through the injector nozzle 23 into the compartment 10 where dry ice is formed to cool the whole of the space within the container. Once the temperature within the container has dropped to the predetermined lower limit of 2° C., the flow of carbon dioxide through the injector nozzle 23 is controlled by the thermostatic device actuated by the spring 24 to maintain the temperature between 2° C. and 6° C.

The carbon dioxide discharged into the compartment 10 may be vented through a gap between the parts 1 and 2 of the container when the container is closed, but preferably a seal is fitted between these two parts to prevent the ingress of dirt and the compartment 10 is provided with a pressure-relief port, which may be fitted with an outlet valve, which opens at a very low positive internal pressure. In this case the outlet port may be connected to an outlet fitting to which a vent pipe may be fixed. This enables carbon dioxide from the container to be exhausted outside a confined space such as the inside of an ambulance.

When the limb has been transported to a hospital, the holder 13 is removed from the container with the limb 17 within it and is transported in the holder 13 to an X-ray machine or directly to an operating theatre.

As well as its cooling effect, the carbon dioxide surrounding the severed body part acts as a bacteriostat and reduces the effects of bacteriological attack. It will not, however, affect enzyme induced decay in the body part.

In some cases it may also be desirable to add a device which ensures that the carbon dioxide is only supplied when the container is in the upright position shown in FIG. 2. This ensures that the carbon dioxide from the syphon tube of the cylinder is discharged from the injection nozzle in the liquid phase. The device then sounds an alarm if this position is not adopted. The device may be gravity-controlled and may be electrically operated.

We claim:

1. A portable container for transporting a severed part of a body and keeping it cool during transport, said container comprising: an openable housing, said housing including heat insulated walls, a holder (13) for holding said body part removably mounted within said housing, a rechargeable cylinder (19) of compressed carbon dioxide mounted to said housing, a shut-off valve (20) on said cylinder, an injector nozzle (23), means (22) connecting said injector nozzle to said shut-off valve, means communicating said nozzle with the inside of said housing for injecting carbon dioxide coolant into said housing to produce dry ice or expanded and cooled gas within said housing, means for venting said housing to atmosphere, and thermostatic means (24) for controlling the flow of said gas through said nozzle into said housing to maintain the temperature in said housing within predetermined limits, wherein said thermostatic means incorporates a spring made of shape-memory alloy, said spring returning from a deformed state to a previous state to open said nozzle when said temperature within said housing rises to an upper one of said predetermined limits.

2. A container as claimed in claim 1, in which said housing comprises two parts, means hingedly connecting said two parts to each other and means fixed to one of said parts defining an external compartment holding said gas cylinder.

3. A container as claimed in claim 2, in which inside faces of said walls of said housing are heat-conducting to act as a heat sink.

4. The container as claimed in claim 3, in which each of said parts comprises a tray of sheet metal having a relatively high coefficient of heat conductivity.

5. A container as claimed in claim 4, in which said trays are selected from Aluminium and Aluminium Alloy.

6. The container as claimed in claim 3, further comprising a covering of high-density plastics foam material moulded on to said walls and covering the whole of the outside surfaces thereof to provide said heat insulation.

7. A container as claimed in claim 6, further comprising an impervious skin of plastics material covering said high-density plastics foam.

8. A container as claimed in claim 4, in which said means defining said compartment includes a metal base-plate, means fixing said base-plate to one side of one of said trays, a holder for said gas cylinder, and means fixing said gas cylinder holder to said base-plate.

9. A container as claimed in claim 8, in which said means defining said compartment further comprise a cover and means detachably fixing said cover to said base-plate, said cover being injection moulded of thermoplastics material and being shaped to form an extension of the outer surface of said housing when said container is closed.

10. A container as claimed in claim 8, further comprising a fitting for receiving said shut-off valve, means mounting said fitting at one end of said compartment, a tube extending from said fitting through said base-plate and through said side wall of said tray into said housing and means fixing said injector nozzle to the end of said tube remote from said fitting.

11. A container as claimed in claim 10, further comprising a baffle and means mounting said baffle within said housing adjacent said injector nozzle to separate said nozzle from direct communication with the remainder of the inside of the said housing.

12. A container as claimed in claim 1, in which said carbon dioxide cylinder is of the syphon tube type.

13. A container as claimed in claim 1, in which said predetermined limits of said temperature are 2° C. and 6° C.

14. A container as claimed in claim 9, further comprising a means defining an opening through said cover and a handle on said shut-off valve, said handle being manually accessible through said opening.

15. A container as claimed in claim 14, further comprising removable seal means said opening, said seal means forming an indentity tag or ring for attachment to said body part.

16. A container as claimed in claim 1, in which said holder for said body part comprises a frame, said frame comprising two parts, means hinging said two parts to each other, and a mesh panel in each of said parts, whereby, when said two parts of said frame are closed together about said hinge means, said body part may be sandwiched between said panels.

17. A portable container for transporting a severed part of a body and keeping it cool during transport, said container comprising: an openable housing, said housing including heat insulated walls, a syphon tube type cylinder (19) of compressed liquid carbon dioxide mounted to said housing, a shut-off valve (20) on said cylinder, a closable injector nozzle (23) located in said housing, means (22) connecting said closable injector nozzle to said shut-off valve such that when said valve is opened liquid carbon dioxide from said cylinder is communicated to said injector nozzle and when said nozzle is open, flows through said nozzle to produce dry ice within said housing, means for venting said housing to atmosphere, and thermostatic means for controlling opening and closing of said injector nozzle to control said flow of said carbon dioxide through said injector nozzle and production of dry ice in said housing to maintain the temperature in said housing within predetermined limits, said thermostatic means incorporating a spring (24) made of a shape-memory alloy, said spring returning from a deformed state to a previous state to open said nozzle when said temperature within said housing rises to an upper one of said predetermined limits.

18. A container as claimed in claim 17, in which said predetermined limits of said temperature are 2° C. and 6° C.

19. A container as claimed in claim 18, further comprising a holder (13) removably mounted within the housing for protectively carrying a severed body part, said holder comprising a foldable frame (14) covered by a flexible mesh (16) for sandwiching said body part when folded.

* * * * *